United States Patent
Chang et al.

(10) Patent No.: US 9,522,971 B2
(45) Date of Patent: Dec. 20, 2016

(54) AMINE MODIFYING MATERIAL AND APPLICATION THEREOF

(71) Applicant: CHUNG YUAN CHRISTIAN UNIVERSITY, Tao-Yuan (TW)

(72) Inventors: Yung Chang, Tao-Yuan (TW); Yan-Wen Chen, Tao-Yuan (TW); Jheng-Fong Jhong, Tao-Yuan (TW)

(73) Assignee: CHUNG YUAN CHRISTIAN UNIVERSITY, Tao-Yuan (TW)

( * ) Notice: Subject to any disclaimer, the term of this patent is extended or adjusted under 35 U.S.C. 154(b) by 0 days.

(21) Appl. No.: 14/587,617

(22) Filed: Dec. 31, 2014

(65) Prior Publication Data

US 2016/0185888 A1    Jun. 30, 2016

(51) Int. Cl.
| | | |
|---|---|---|
| *C07K 1/22* | (2006.01) | |
| *C07K 14/765* | (2006.01) | |
| *C07K 14/75* | (2006.01) | |
| *C08F 220/34* | (2006.01) | |

(52) U.S. Cl.
CPC ............... *C08F 220/34* (2013.01); *C07K 1/22* (2013.01); *C07K 14/75* (2013.01); *C07K 14/765* (2013.01)

(58) Field of Classification Search
CPC .............................. B01D 39/083; B01D 15/36
See application file for complete search history.

(56) References Cited

U.S. PATENT DOCUMENTS 5,407,581 A * 4/1995 Onodera ............ B01D 39/1623
210/321.69

OTHER PUBLICATIONS

Zhou et al, Environmental Science and Technology, High-Throughput Membrane Surface Modification to Control NOM Fouling, 2009, 43, 3865-3871.*

* cited by examiner

*Primary Examiner* — Paul A Zucker
(74) *Attorney, Agent, or Firm* — WPAT, PC; Justin King

(57) ABSTRACT

The present invention discloses an amine modifying material which is a copolymer polymerized from an amine functional acrylate, a poly(ethylene glycol) functional acrylate and a cross-linker. The application of the amine modifying material in the bio-molecules separation area is also provided in the present invention.

5 Claims, 5 Drawing Sheets

AMINE MODIFYING MATERIAL AND APPLICATION THEREOF

BACKGROUND OF THE INVENTION

1. Field of the Invention

This invention relates to the field of a hydrogel, and more particularly, to an amine modifying hydrogel and application thereof.

2. Description of the Prior Art

In general, a hydrogel is a network of polymer chains that are hydrophilic and also possess a degree of flexibility very similar to natural tissue, due to their significant water content.

PEG-based hydrogels have been prepared using Michael-type addition reaction such as, PEG-thiol or PEG-amine reacting with PEG-activated ester (NHS) or PEG-acrylate. The reactions can result in unwanted small molecules as a secondary by product. Similarly, PEG-based hydrogels have been prepared using 4-arm PEG-vinylsulfone and linear PEG-estersulfhydryl. However, such PEG-based hydrogels absorb too quickly, within 5 days (S. Zustiak and J. Leach, "Hydrolytically Degradable Poly(Ethylene Glycol) Hydrogel Scaffolds with Tunable Degradation and Mechanical Properties", Biomacromolecules 2010, 11, 1348-1357).

Gunavadhi et al. discloses a method for electrophoretic separation of protein by employing carbon nanotube-modified polyacrylamide gels. (Electrophoresis 2012; 33(8) 1271). Schmaljohann et al. discloses a thermo-responsive hydrogel based on a poly(NiPAAm-co-PEGMA) precursor. The material has been demonstrated to show a temperature-induced change in cell adhesion and detachment behavior. It can be utilized in smart cell culture carrier with different substrate chemistry in a lateral resolution reflecting the dimensions of the cells. (Polymer Preprints 45, 380-381,)

U.S. Pat. No. 7,857,447 disclose hydrogels comprising a hydrophilic telechelic macromonomer selected from poly-ethylene glycol-diacrylate or dimethacrylate, interpenetrated with a second hydrophilic network of crosslinked poly-acrylic acid. The hydrogels have high oxygen permeability, strength, water content, and resistance to protein adsorption. However, the hydrogels is designed to serve as a contact lens.

US 2006/0141045 disclose spheroidal beads present an exterior surface of a hydrophilic hydrogel, which is an isocyanate-functional polymer that is polymerized by urethane bonds and cross-linked by urethane and urea bonds and the beads is applied for the separation of cells.

Based on the aforementioned, the important target of current bio-industries is to develop a material and the related method that can simply achieving the selective separation of biomolecules such as proteins and blood cells.

SUMMARY OF THE INVENTION

In accordance with the present invention, an amine modifying material and application thereof substantially obviates one or more of the problems resulted from the limitations and disadvantages of the prior art mentioned in the background.

One of the objectives in the present invention is to disclose an amine modifying material. The amine modifying material is a copolymer polymerized from an amine functional monomer, a poly(ethylene glycol) functional monomer and a cross-linker containing at least two alkene groups. The amine modifying material is positively charged so as to adhere to negatively charged bio-molecules by electrostatic force. Furthermore, the kinds of the amine functional monomer and the amine percentage of the amine modifying material play an important role to control the properties and application of the amine modifying material. The aforementioned amine percentage of the amine modifying material is controlled by adjusting the molar ratio between the amine functional monomer and the poly(ethylene glycol) functional monomer. Additionally, the cross-linker is mainly applied to form the material network structure. Preferably, the amine modifying material is a hydrogel.

In one embodiment, the amine functional monomer is the tertiary amine functional acrylate consisting of the following chemical structure of formula (I), where $R_1$ is H or $CH_3$; $R_2$ is O or NH and m is an integer of 1-5. Preferably, $R_1$ is $CH_3$ and $R_2$ is O. The representative tertiary amine functional acrylate is dimethylaminoethyl methacrylate.

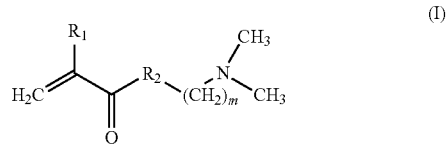

(I)

In one embodiment, the amine functional monomer is the quaternary ammonium salt functional acrylate consisting of the following chemical structure of formula (II), where $R_1$ is H or $CH_3$; $R_2$ is O or NH and m is an integer of 1-5. Preferably, $R_1$ is $CH_3$ and $R_2$ is O. The representative quaternary ammonium salt functional acrylate is [2-(meth-acryloyloxy)ethyl]trimethylammonium chloride.

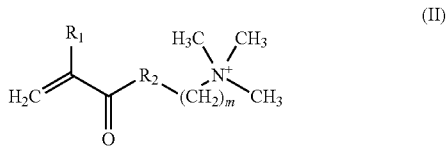

(II)

In another embodiment, the poly(ethylene glycol) functional monomer is selected from one or the combination of the group consisting of methoxy poly(ethylene glycol) methacrylate and methoxy poly(ethylene glycol) acrylate.

Another objective of the present invention is to provide a method for removing leukocytes from a blood sample. The method comprises the following step: providing a blood sample containing leukocytes; providing an amine modifying material, wherein the amine modifying material is a copolymer polymerized from an amine functional monomer, a poly(ethylene glycol) functional monomer and a cross-linker containing at least two alkene groups; treating the blood sample with the amine modifying material; and the leukocytes adhere onto the surface of the amine modifying material so as to remove the leukocytes from the blood sample. The mechanism of the removing leukocytes from the blood sample is that the surface of the amine modifying material is positively charged so as to adhere to the negatively charged leukocytes. In a specific range of the amine percentage of the amine modifying material, the aforementioned amine modifying material adhere leukocytes much more than platelets and erythrocytes so the leukocytes are selectively removed from the blood sample. Preferably, the amine modifying material is a hydrogel.

In one embodiment, the amine functional monomer is the tertiary amine functional acrylate consisting of the following chemical structure of formula (I), where $R_1$ is H or $CH_3$; $R_2$ is O or NH and m is an integer of 1-5. Preferably, $R_1$ is $CH_3$ and $R_2$ is O. The representative tertiary amine functional acrylate is dimethylaminoethyl methacrylate.

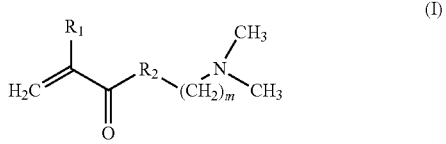

In one embodiment, the amine functional monomer is the quaternary ammonium salt functional acrylate consisting of the following chemical structure of formula (II), where $R_1$ is H or $CH_3$; $R_2$ is 0 or NH and m is an integer of 1-5. Preferably, $R_1$ is $CH_3$ and $R_2$ is O. The representative quaternary ammonium salt functional acrylate is [2-(methacryloyloxy)ethyl]trimethylammonium chloride.

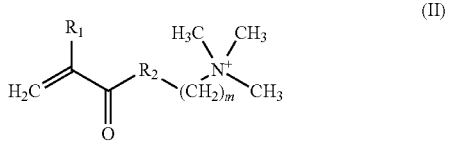

In another embodiment, the poly(ethylene glycol) functional monomer is selected from one or the combination of the group consisting of methoxy poly(ethylene glycol) methacrylate and methoxy poly(ethylene glycol) acrylate.

In yet another embodiment, the amine modifying material is the copolymer polymerized from dimethylaminoethyl methacrylate, methoxy poly(ethylene glycol) methacrylate has an average molecular weight between 400 and 600 Daltons and N,N-Methylenebisacrylamide. The aforementioned amine modifying material has the amine percentage being between 51% and 75% and adhere leukocytes much more than platelets and erythrocytes.

In another embodiment, the amine modifying material is the copolymer polymerized from [2-(methacryloyloxy) ethyl]trimethylammonium chloride, methoxy poly(ethylene glycol) methacrylate has an average molecular weight between 400 and 600 Daltons and N,N-Methylenebisacrylamide. The aforementioned amine modifying material has the amine percentage being between 39% and 50% and adhere leukocytes much more than platelets and erythrocytes.

Still another objective of the present invention is to provide a method for separating a protein from a platelet poor plasma solution. The method for separating a protein from a platelet poor plasma solution comprising: providing a platelet poor plasma solution containing a gamma-globulin, a fibrinogen and a human serum albumin; providing an amine modifying material, wherein the amine modifying material is a copolymer polymerized from an amine functional monomer, a poly(ethylene glycol) functional monomer and a cross-linker containing at least two alkene groups; and treating the platelet poor plasma solution with the amine modifying material. Preferably, the amine modifying material is a hydrogel.

In one embodiment, the amine functional monomer is the tertiary amine functional acrylate consisting of the following chemical structure of formula (I), where $R_1$ is H or $CH_3$; $R_2$ is O or NH and m is an integer of 1-5. Preferably, $R_1$ is $CH_3$ and $R_2$ is O. The representative tertiary amine functional acrylate tertiary amine functional acrylate is dimethylaminoethyl methacrylate.

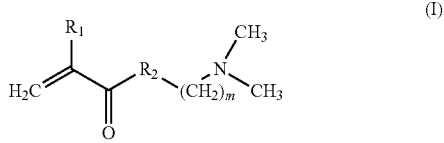

In one embodiment, the amine functional monomer is the quaternary ammonium salt functional acrylate consisting of the following chemical structure of formula (II), where $R_1$ is H or $CH_3$; $R_2$ is O or NH and m is an integer of 1-5. Preferably, $R_1$ is $CH_3$ and $R_2$ is O. The representative quaternary ammonium salt functional acrylate is [2-(methacryloyloxy)ethyl]trimethylammonium chloride.

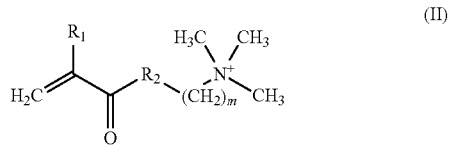

In another embodiment, the poly(ethylene glycol) functional monomer is selected from one or the combination of the group consisting of methoxy poly(ethylene glycol) methacrylate and methoxy poly(ethylene glycol) acrylate.

To achieve selective removing different kinds of the protein from the platelet poor plasma solution, the amine percentage of the amine modifying material is a critical parameter and controlled by adjusting the molar ratio between the amine functional monomer and the poly(ethylene glycol) functional monomer. In a specific range of the amine percentage of the amine modifying material, the fibrinogen and the human serum albumin are separated from the platelet poor plasma solution, respectively.

In one embodiment, the human serum albumin is separated by treating the platelet poor plasma solution with the amine modifying material has an amine percentage between 70% and 80%.

In another embodiment, the fibrinogen is separated by treating the platelet poor plasma solution with the amine modifying material has an amine percentage between 26% and 65%.

Accordingly, the present invention discloses an amine modifying material which is a copolymer polymerized from an amine functional monomer, a poly(ethylene glycol) functional monomer and a cross-linker containing at least two alkene groups. The amine modifying hydrogel is positively charged so as to adhere to negatively charged bio-molecules by electrostatic force. Secondly, the aforementioned amine modifying material has an specific range of the amine percentage is able to selectively separate the bio-molecules. Therefore, the present invention also provides a method for removing leukocytes from a blood sample and a method for separating a protein from a platelet poor plasma solution.

BRIEF DESCRIPTION OF THE DRAWINGS

The accompanying drawings incorporated in and forming a part of the specification illustrate several aspects of the present invention, and together with the description serve to explain the principles of the disclosure. In the drawings.

DETAILED DESCRIPTION OF THE PREFERRED EMBODIMENTS

Figure 1:
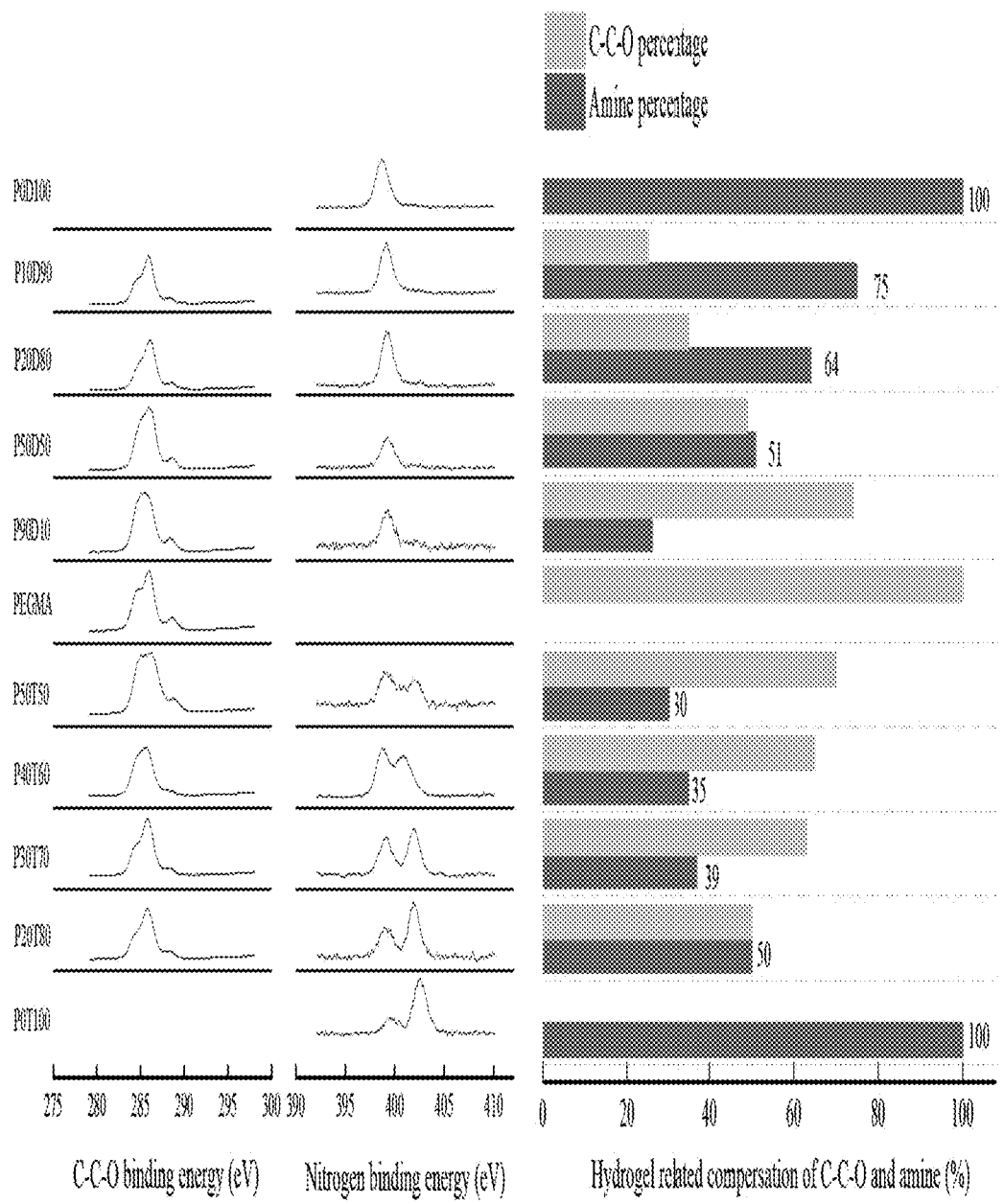
FIG. 1 shows a XPS spectra of the hydrogel surfaces with DMAEMA-PEGMA brushes or TMA-PEGMA brushes in the N and C—C—O regions of samples PEGMA/DMAEMA and PEGMA/TMA.

What is probed into the invention is an amine modifying material and application thereof. Detail descriptions of the structure and elements will be provided in the following in order to make the invention thoroughly understood. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, an amine modifying material is disclosed. The amine modifying material is a copolymer polymerized from an amine functional monomer, a poly(ethylene glycol) functional monomer and a cross-linker containing at least two alkene groups. The amine modifying material is positively charged so as to adhere to negatively charged bio-molecules by electrostatic force. Furthermore, the kinds of the amine functional monomer and the amine percentage of the amine modifying material play an important role to control the properties and application of the amine modifying material. The aforementioned amine percentage of the amine modifying material is controlled by adjusting the molar ratio between the amine functional monomer and the poly(ethylene glycol) functional monomer. Additionally, the cross-linker is mainly applied to form the network structure. Preferably, the amine modifying material is a hydrogel.

The amine percentage of the amine modifying material is determined by XPS spectra from the spectral area of the C—C—O binding energy at 285 eV, the tertiary nitrogen binding energy at 399 eV and quaternary amine binding energy at 403 eV, respectively.

In one embodiment, the amine functional monomer is the tertiary amine functional acrylate consisting of the following chemical structure of formula (I), where $R_1$ is H or $CH_3$; $R_2$ is O or NH and m is an integer of 1-5. Preferably, $R_1$ is $CH_3$ and $R_2$ is O. The representative tertiary amine functional acrylate is dimethylaminoethyl methacrylate.

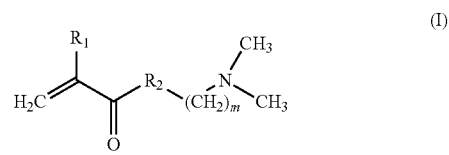

In one embodiment, the amine functional monomer is the quaternary ammonium salt functional acrylate has an following chemical structure of formula (II), where $R_1$ is H or $CH_3$; $R_2$ is O or NH and m is an integer of 1-5. Preferably, $R_1$ is $CH_3$ and $R_2$ is O. The representative quaternary ammonium salt functional acrylate is [2-(methacryloyloxy)ethyl]trimethylammonium chloride.

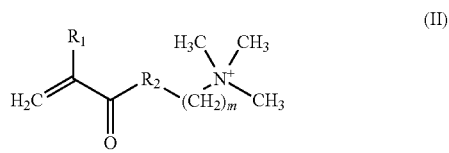

In another embodiment, the poly(ethylene glycol) functional monomer is selected from one or the combination of the group consisting of methoxy poly(ethylene glycol) methacrylate and methoxy poly(ethylene glycol) acrylate.

In one example of the first embodiment, the amine modifying material is the copolymer polymerized from dimethylaminoethyl methacrylate, methoxy poly(ethylene glycol) methacrylate has an average molecular weight between 400 and 600 Daltons and N,N-Methylenebisacrylamide and the amine percentage of the copolymer is between 20% and 80%.

Preferably, the amine modifying material is the copolymer polymerized from dimethylaminoethyl methacrylate, methoxy poly(ethylene glycol) methacrylate has an average molecular weight of 500 Daltons and N,N-Methylenebisacrylamide.

In another example of the first embodiment, the amine modifying material is the copolymer polymerized from [2-(methacryloyloxy)ethyl]trimethylammonium chloride, methoxy poly(ethylene glycol) methacrylate has an average molecular weight between 400 and 600 Daltons and N,N-Methylenebisacrylamide and the amine percentage of the copolymer is between 30% and 50%.

Preferably, the amine modifying material is the copolymer polymerized from [2-(methacryloyloxy)ethyl]trimethylammonium chloride, methoxy poly(ethylene glycol) methacrylate has an average molecular weight of 500 Daltons and N,N-Methylenebisacrylamide.

In a second embodiment of the present invention, a method for removing leukocytes from a blood sample is provided. The method comprises the following step: providing a blood sample containing leukocytes; providing an amine modifying material, wherein the amine modifying material is a copolymer polymerized from an amine functional monomer, a poly(ethylene glycol) functional monomer and a cross-linker containing at least two alkene groups;

treating the blood sample with the amine modifying material; and the leukocytes adhere onto the surface of the amine modifying material so as to remove the leukocytes from the blood sample. Preferably, the amine modifying material is a hydrogel.

The mechanism of the removing leukocytes from the blood sample is that the surface of the amine modifying material is positively charged so as to adhere to the negatively charged leukocytes. In a specific range of the amine percentage of the amine modifying material, the aforementioned amine modifying material adhere leukocytes much more than platelets and erythrocytes so the leukocytes are selectively removed from the blood sample.

In one embodiment, the amine functional monomer is the tertiary amine functional acrylate consisting of the following chemical structure of formula (I), where $R_1$ is H or $CH_3$; $R_2$ is O or NH and m is an integer of 1-5. Preferably, $R_1$ is $CH_3$ and $R_2$ is O. The representative tertiary amine functional acrylate is dimethylaminoethyl methacrylate.

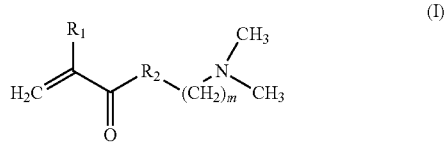

(I)

In one embodiment, the amine functional monomer is the quaternary ammonium salt functional acrylate consisting of the following chemical structure of formula (II), where $R_1$ is H or $CH_3$; $R_2$ is O or NH and m is an integer of 1-5. Preferably, $R_1$ is $CH_3$ and $R_2$ is O. The representative quaternary ammonium salt functional acrylate is [2-(methacryloyloxy)ethyl]trimethylammonium chloride.

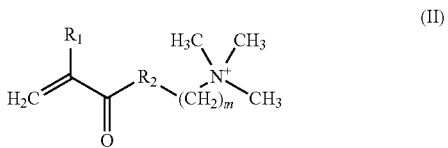

(II)

In another embodiment, the poly(ethylene glycol) functional monomer is selected from one or the combination of the group consisting of methoxy poly(ethylene glycol) methacrylate and methoxy poly(ethylene glycol) acrylate.

In yet another embodiment, the amine modifying material is the copolymer polymerized from dimethylaminoethyl methacrylate, methoxy poly(ethylene glycol) methacrylate has an average molecular weight between 400 and 600 Daltons and N,N-Methylenebisacrylamide. The aforementioned amine modifying material has the amine percentage being between 51% and 75%/u and adhere leukocytes much more than platelets and erythrocytes.

In another embodiment, the amine modifying material is the copolymer polymerized from [2-(methacryloyloxy)ethyl]trimethylammonium chloride, methoxy poly(ethylene glycol) methacrylate has an average molecular weight between 400 and 600 Daltons and N,N-Methylenebisacrylamide. The aforementioned amine modifying material has the amine percentage being between 39% and 50% and adhere leukocytes much more than platelets and erythrocytes.

In a third embodiment of the present invention, a method for separating a protein from a platelet poor plasma solution is provided. The method for separating a protein from a platelet poor plasma solution comprising: providing a platelet poor plasma solution containing a gamma-globulin, a fibrinogen and a human serum albumin; providing an amine modifying material, wherein the amine modifying material is a copolymer polymerized from an amine functional monomer, a poly(ethylene glycol) functional monomer and a cross-linker containing at least two alkene groups; and treating the platelet poor plasma solution with the amine modifying material. Preferably, the amine modifying material is a hydrogel.

In one embodiment, the amine functional monomer is the tertiary amine functional acrylate consisting of the following chemical structure of formula (I), where $R_1$ is H or $CH_3$; $R_2$ is O or NH and m is an integer of 1-5. Preferably, $R_1$ is $CH_3$ and $R_2$ is O. The representative tertiary amine functional acrylate is dimethylaminoethyl methacrylate.

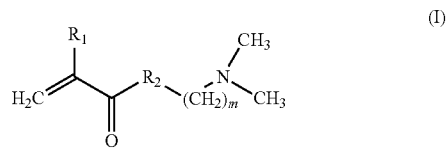

(I)

In one embodiment, the amine functional monomer is the quaternary ammonium salt functional acrylate consisting of the following chemical structure of formula (II), where $R_1$ is H or $CH_3$; $R_2$ is O or NH and m is an integer of 1-5. Preferably, $R_1$ is $CH_3$ and $R_2$ is O. The representative quaternary ammonium salt functional acrylate is [2-(methacryloyloxy)ethyl]trimethylammonium chloride.

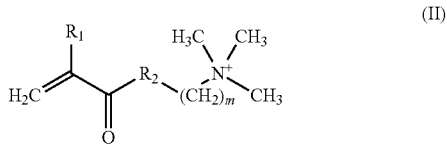

(II)

In another embodiment, the poly(ethylene glycol) functional monomer is selected from one or the combination of the group consisting of methoxy poly(ethylene glycol) methacrylate and methoxy poly(ethylene glycol) acrylate.

In one example of the third embodiment, the amine modifying material is the copolymer polymerized from dimethylaminoethyl methacrylate, methoxy poly(ethylene glycol) methacrylate has an average molecular weight between 400 and 600 Daltons and N,N-Methylenebisacrylamide.

In another example of the third embodiment, the amine modifying material is the copolymer polymerized from [2-(methacryloyloxy)ethyl]trimethylammonium chloride, methoxy poly(ethylene glycol) methacrylate has an average molecular weight between 400 and 600 Daltons and N,N-Methylenebisacrylamide.

To achieve selective removing different kinds of the protein from the platelet poor plasma solution, the amine percentage of the amine modifying material is a critical parameter and controlled by adjusting the molar ratio between the amine functional monomer and the poly(ethylene glycol) functional monomer. In a specific range of the amine percentage of the amine modifying material, the fibrinogen and the human serum albumin are separated from the platelet poor plasma solution, respectively.

In one embodiment, the human serum albumin is separated by treating the platelet poor plasma solution with the amine modifying material has an amine percentage between 70% and 80%.

In another embodiment, the fibrinogen is separated by treating the platelet poor plasma solution with the amine modifying material has an amine percentage between 26% and 65%.

In accordance with the foregoing summary, the following presents a detailed description of the example of the present invention, which is presently considered the best mode thereof. However, this invention can also be applied extensively to other embodiments, and the scope of this present invention is expressly not limited except as specified in the accompanying claims Example 1

The synthesis of the amine modifying hydrogel I polymerized from dimethylaminoethyl methacrylate (DMAEMA), methoxy poly(ethylene glycol) methacrylate (PEGMA) has an average molecular weight of 500 Daltons and N,N-Methylenebisacrylamide.

The amine modifying hydrogel I polymerized from dimethylaminoethyl methacrylate (DMAEMA), and methoxy poly(ethylene glycol) methacrylate (PEGMA) has an average molecular weight of 500 Daltons is synthesized where "m" and "n" represent the molar ratio of P to D, respectively. For example, amine modifying hydrogel I: P20D80 represents the molar ratio of PEGMA to DMAEMA is 20:80. The same representation is also used in the following.

Dimethylaminoethyl methacrylate (DMAEMA) and methoxy poly(ethylene glycol) methacrylate (PEGMA) has an average molecular weight of 500 Daltons with a different molar ratio were taken and blended until uniform. Then, a cross-linker N,N-Methylenebisacrylamide (NMBA) and an initiator APS (Ammonium peroxodisulfate) were added into the mixture of DMAEMA and PEGMA (monomer raw material) to make the mixture of DMAEMA and PEGMA be 90 wt %, NMBA be 8 wt %, and APS be 2 wt %. At room temperature (25° C.), monomers and the cross-linker underwent free radical polymerization.

Finally, a catalyst TEMED (N,N,N',N'-Teramethyl ethylenediamine) was added (1 wt %) to speed up the reaction. The reaction mixture was then taken out and placed in a mold for preparing amine modifying hydrogel I for being completely reacted to form amine modifying hydrogel I. After reacted for two hours, amine modifying hydrogel I was taken out to be dipped into de-ionized water and stored in a 4° C. refrigerator. Every 24 hours, de-ionized water was used to wash amine modifying hydrogel I three times to ensure cleanness of storage environment of amine modifying hydrogel I. The amine modifying hydrogel I was ready for the blood cell adhesion study and the proteins adsorption study.

Example 2

The synthesis of the amine modifying hydrogel II polymerized from [2-(methacryloyloxy)ethyl]trimethylammonium chloride (TMA), methoxy poly(ethylene glycol) methacrylate (PEGMA) has an average molecular weight of 500 Daltons and N,N-Methylenebisacrylamide.

The amine modifying hydrogel II polymerized from [2-(methacryloyloxy)ethyl]trimethylammonium chloride (TMA), and methoxy poly(ethylene glycol) methacrylate (PEGMA) has an average molecular weight of 500 Daltons is synthesized where "m" and "n" represent the molar ratio of P to T, respectively. For example, amine modifying hydrogel II: P20T80 represents the molar ratio of PEGMA to TMA is 20:80. The same representation is also used in the following.

[2-(methacryloyloxy)ethyl]trimethylammonium chloride (TMA) and methoxy poly(ethylene glycol) methacrylate (PEGMA) has an average molecular weight of 500 Daltons with a different molar ratio were taken and blended until uniform. Then, a cross-linker N,N-Methylenebisacrylamide (NMBA) and an initiator APS (Ammonium peroxodisulfate) were added into the mixture of TMA and PEGMA (monomer raw material) to make the mixture of TMA and PEGMA be 90 wt %, NMBA be 8 wt %, and APS be 2 wt %. At room temperature (25° C.), monomers and the cross-linker underwent free radical polymerization. Finally, a catalyst TEMED (N,N,N',N'-Teramethylethylenediamine) was added (1 wt %) to speed up the reaction. The reaction mixture was then taken out and placed in a mold for preparing amine modifying hydrogel II for being completely reacted to form amine modifying hydrogel II. After reacted for two hours, amine modifying hydrogel II was taken out to be dipped into de-ionized water and stored in a 4° C. refrigerator. Every 24 hours, de-ionized water was used to wash amine modifying hydrogel II three times to ensure cleanness of storage environment of amine modifying hydrogel II. The amine modifying hydrogel II was ready for the blood cell adhesion study and the proteins adsorption study.

The amine percentage of the amine modifying hydrogel is determined by XPS spectra from the spectral area of the C—C—O binding energy at 285 eV, the tertiary nitrogen binding energy at 399 eV and quaternary amine binding energy at 403 eV, respectively. The amine percentage of the amine modifying hydrogel synthesized from example 1 and example 2 is shown as TABLE 1.

TABLE 1

| amine modifying hydrogel | Amine percentage % |
| --- | --- |
| P90D10 | 26 |
| P50D50 | 51 |
| P20D80 | 64 |
| P10D90 | 75 |
| P50T50 | 30 |
| P40T60 | 35 |
| P30T70 | 39 |
| P20T80 | 50 |

Example 3

The Study of the Blood Cell Adhesion on the PEGMA Hydrogel

The PEGMA hydrogels has an average molecular weight of 300, 500 and 950Daltons were evaluated for the blood cell adhesion ability, respectively. The PEGMA hydrogel samples were placed in individual wells of a 24-well tissue culture plate, and each well was equilibrated with 1000 μL of phosphate buffered solution (PBS) for 1 hour at 37° C. Blood was obtained from a healthy human volunteer. White Blood Cells Concentrate (WBC), Platelet rich plasma (PRP), Red blood cells (RBCs) was prepared by centrifugation of the blood at 1200 rpm for 10 min. For the test of blood cell adhesion on the PEGMA hydrogel, 200 μL aliquots of the blood solution were directly placed on the amine modifying hydrogel surface in each well of the tissue culture plate and incubated for 120 min at 37° C.

After the cell adhesion, the PEGMA hydrogels were rinsed twice with 1000 μL of PBS, they were immersed in 2.5% glutaraldehyde of PBS for 24 hours at 4 C to fix the adhered cells. Finally, the samples observation under Nikon A1R confocal operating at 488 nm and use software named Image J to quantify the number of cell adhesion on the surface of the amine PEGMA hydrogels.

Figure 2:
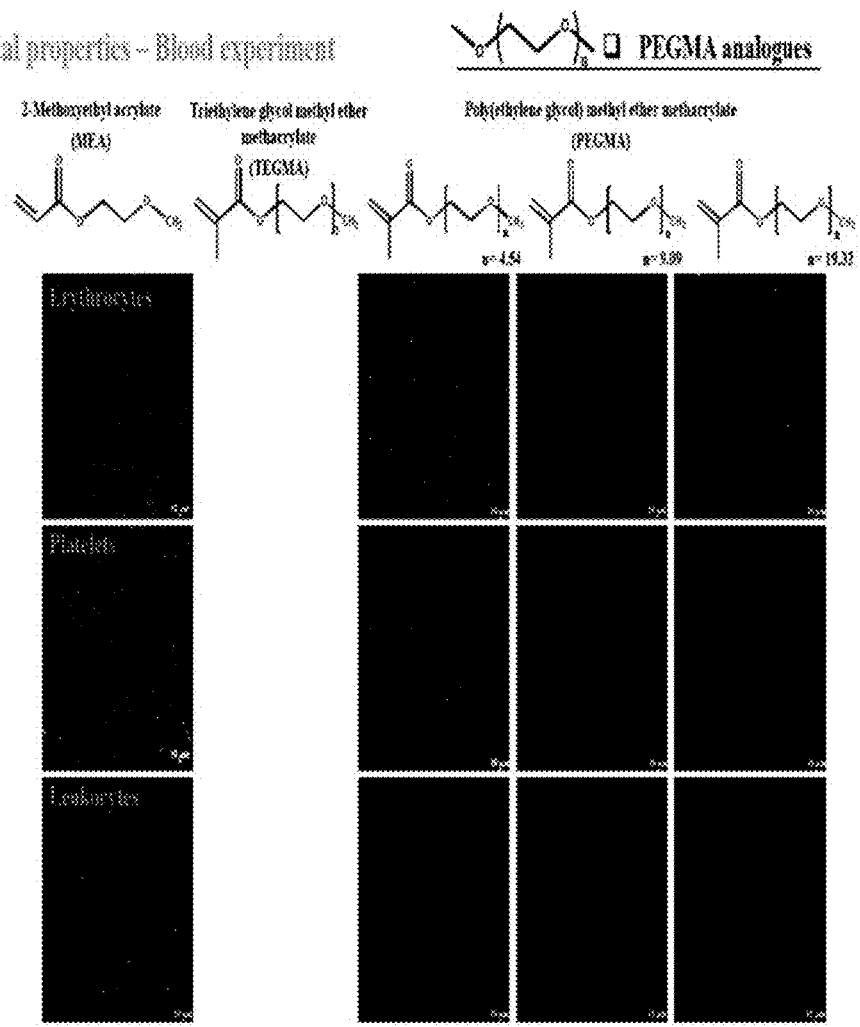
FIG. 2 shows a Confocal Laser Scanning Microscopic Images of the platelet, erythrocyte, and leukocyte adhesion test on the surface of the PEGMA has an average numbers of ethylene glycol of 4.04, 9.09 and 19.32 respectively.
Figure 3:
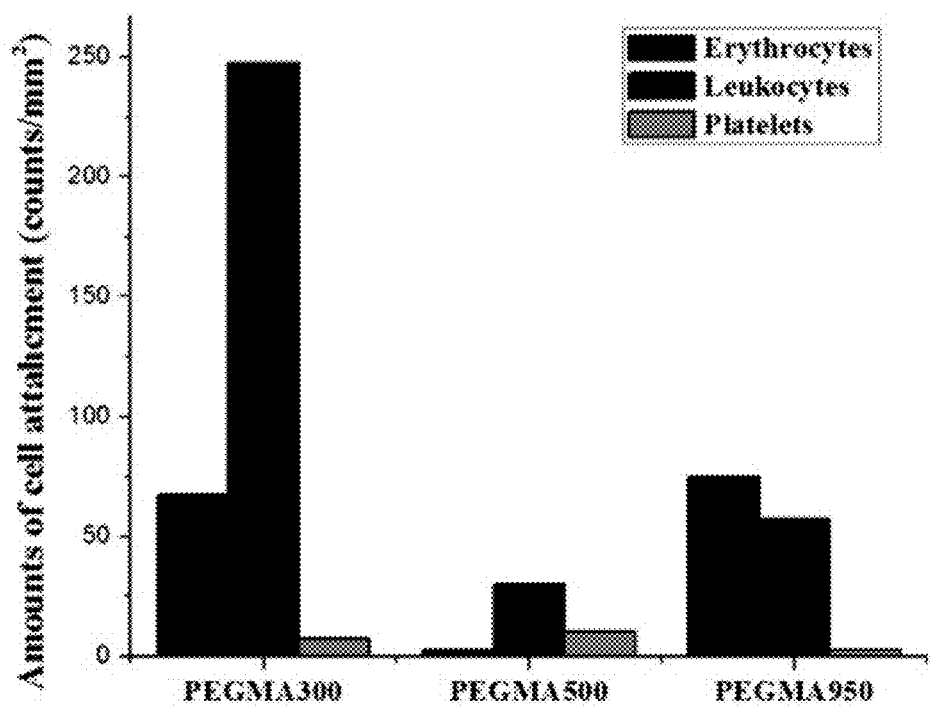
FIG. 3. shows a bar graph illustrating the experimental results of platelet, erythrocyte, and leukocyte adhesion with different average molecule weight of the PEGMA according to the example 3 of the present invention.

The experimental results as shown FIG. 2 surprisingly shows the PEGMA hydrogel has an average molecular weight of 500 Daltons (the average numbers of ethylene glycol is 9.09) almost does not capture any erythrocytes. In contrast, the PEGMA hydrogel has an average molecular weight of 300 Daltons (the average numbers of ethylene glycol is 4.04) and 950 Daltons (the average numbers of ethylene glycol is 19.32) capture erythrocytes. Accordingly, the PEGMA hydrogel has an average molecular weight of 500 Daltons is an excellent material for selective removing leukocytes from a blood sample.

Example 4

The study of the blood cell adhesion on the amine modifying hydrogels obtained from example 1 and example 2.

The amine modifying hydrogel sample were placed in individual wells of a 24-well tissue culture plate, and each well was equilibrated with 1000 μL of phosphate buffered solution (PBS) for 2 hours at 25° C. Blood was obtained from a healthy human volunteer. White Blood Cells Concentrate (WBC), Platelet rich plasma (PRP), Red blood cells (RBCs) was prepared by centrifugation of the blood at 1200 rpm for 10 min. For the test of blood cell adhesion on the amine modifying hydrogel, 200 μL aliquots of the blood solution were directly placed on the amine modifying hydrogel surface in each well of the tissue culture plate and incubated for 120 min at 37° C.

After the cell adhesion, the amine modifying hydrogels were rinsed twice with 1000 μL of PBS, they were immersed in 2.5% glutaraldehyde of PBS for 48 h at 4° C. to fix the adhered cells. Finally, the samples observation under Nikon A1R confocal operating at 488 nm and use software named Image J to quantify the number of cell adhesion on the surface of the amine modifying hydrogels.

Figure 4:
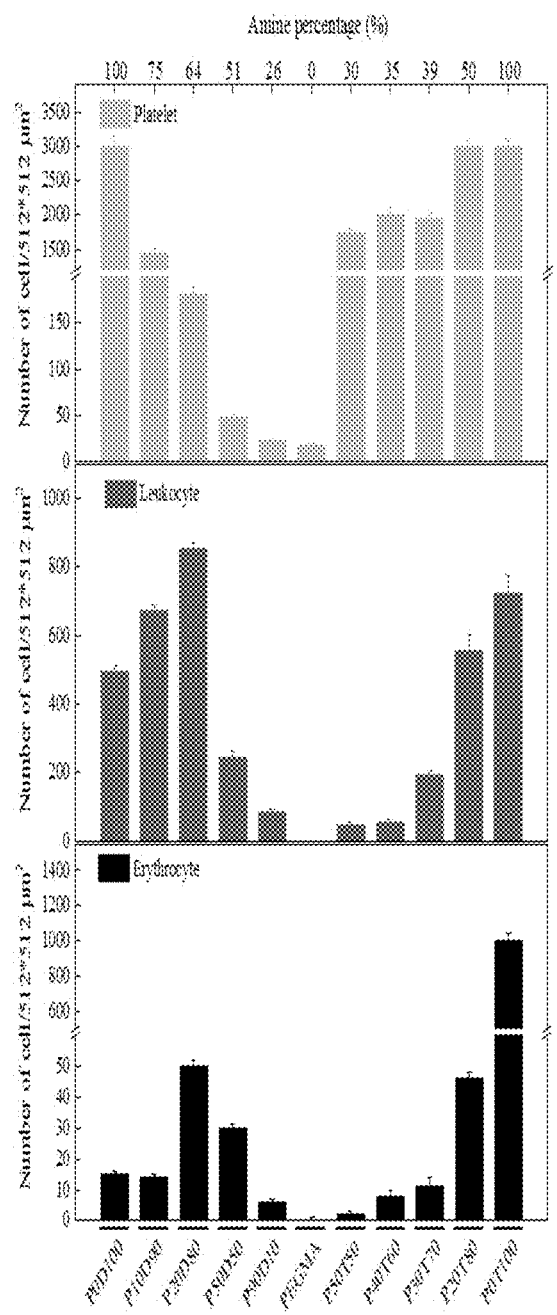
FIG. 4. shows a bar graph illustrating the experimental results of platelet, erythrocyte, and leukocyte adhesion with different amine percentage of the amine modifying hydrogel according to the example 4 of the present invention.

The experimental results of the platelets, the erythrocytes, and the leukocytes adhesion with different amine percentage of the amine modifying hydrogels is shown in FIG. 4. The amine modifying hydrogel has an amine percentage of 64% (P20D80) adhere much more the leukocytes onto its surface than the platelets and the erythrocytes. When the amine percentage of the amine modifying hydrogel is more than 75%, the number of the platelets adhering onto the surface of the amine modifying hydrogel increase quickly but the number of the leukocytes adhering onto the surface of the amine modifying hydrogel decrease.

In the specific range of the amine percentage between 39% and 75%, the number of the erythrocytes adhering onto the surface of the amine modifying hydrogel is less than the number of the leukocytes adhering onto the surface of the amine modifying hydrogel. Hence, the leukocytes are selectively removed from the blood sample due to the stronger adhering leukocytes ability of the amine modifying hydrogel has an specific range of the amine percentage, such as the amine modifying hydrogel has an amine percentage of 64% (P20D80).

Example 5

The study of the protein adsorption on the amine modifying hydrogels obtained from example 1 and example 2.

In this study, platelet poor plasma (PPP) solution containing plasma proteins was tested on the amine modifying hydrogel surface. Blood was obtained from a healthy human volunteer. PPP was prepared by centrifugation of the blood at 3000 rpm for 10 min.

The adsorption of human plasma solution of human serum albumin, gamma-globulin, and fibrinogen on the amine modifying hydrogels obtained from example 1 and example 2 were evaluated, respectively, using the enzyme-linked immunosorbent assay (ELISA) according to the standard protocol as described briefly below.

First, the membranes of 0.4 cm$^2$ surface areas were placed in individual wells of a 24-well tissue culture plate, and each well was equilibrated with 1000 μL of PBS for 60 min at 37 C. Then, the amine modifying hydrogel were soaked in 500 μL of 100% platelet poor plasma (PPP) solution. After 180 min of incubation at 37 C, the films were rinsed five times with 500 μL of PBS and then incubated in bovine serum albumin (BSA, purchased from Aldrich) for 90 min at 37° C. to block the areas unoccupied by protein. The amine modifying hydrogels were rinsed with PBS five times more, transferred to a new plate, and incubated in a 500 μL PBS solution.

The membranes were incubated with primary monoclonal antibody that reacted with the human plasma protein (i.e., human serum albumin or fibrinogen) for 90 min at 37 C and then blocked with 10 mg/mL BSA in PBS solution for 24 h at 37 C. The hydrogel were subsequently incubated with the secondary monoclonal antibody, horseradish peroxidase (HRP)-conjugated immunoglobulins for 60 min at 37 C. The primary antibody was not used, and only the secondary antibody (goat F(ab)2 antihuman immunoglobulin peroxidase conjugate antibody) treatment was performed for the assay of the amount of human gamma-globulin adsorbed on the membranes from PPP solution for 90 min at 37 C.

The amine modifying hydrogels were rinsed five times with 500 μL of PBS and transferred into clean wells, followed by the addition of 500 μL of PBS containing 1 mg/mL chromogen of 3,30,5,50-tetramethylbenzidine, 0.05 wt % Tween 20, and 0.03 wt % hydrogen peroxide. After incubation for 20 min at 37 C, the enzyme induced color reaction was stopped by adding 500 μL of 1 mmol/mL $H_2SO_4$ to the solution in each well, and finally, the absorbance of light at 450 nm was determined by a micro-plate reader. Protein adsorption on the amine modifying hydrogels was normalized with respect to that on the virgin PS as a reference. These measurements were carried out 6 times for each hydrogel (n=6).

Figure 5:
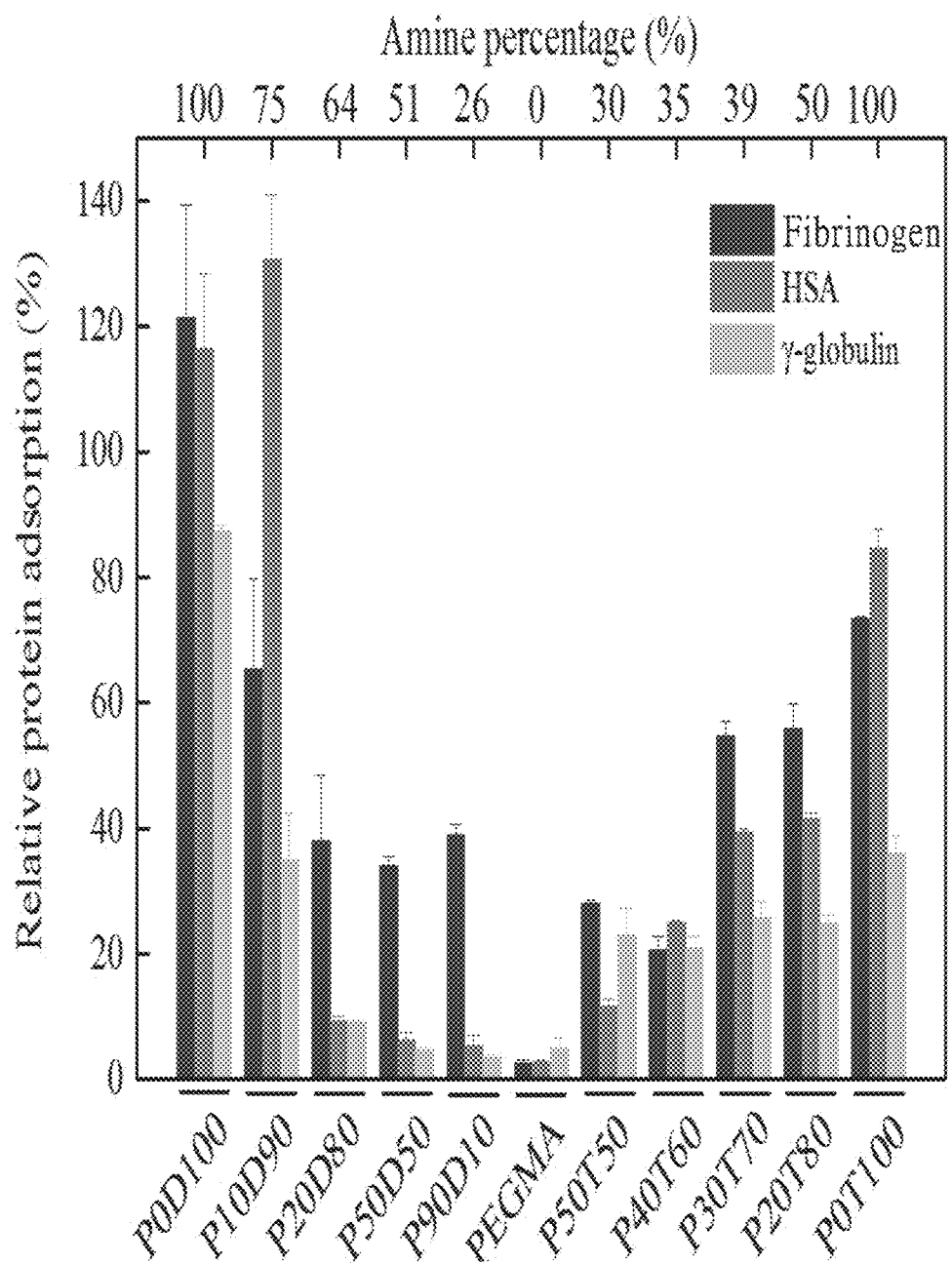
FIG. 5. shows a bar graph illustrating the experimental results of gamma globulin, fibrinogen, and human serum albumin(HSA) adsorption with different amine percentage of the amine modifying hydrogel according to the example 5 of the present invention.

The experimental results of the various proteins adsorption with different amine percentage of the amine modifying hydrogel is shown in FIG. 5. The amine modifying hydrogel has an amine percentage of 75% (P10D90) show the relative human serum albumin (HSA) adsorption is about 130% and is much more than the relative gamma globulin adsorption and the relative fibrinogen adsorption. As the amine modifying hydrogel have an amine percentage between 26% and 64%, the relative fibrinogen adsorption is more than the relative gamma globulin adsorption and the relative human serum albumin adsorption.

In contrast, the hydrogel (PEGMA) is not the amine modifying hydrogel and show excellent non-fouling properties without selectivity in the protein adsorption study. Accordingly, the amine modifying hydrogel having different amine percentage show unobvious and unpredictable behaviors in the various proteins adsorption and is an excellent material for using in the protein separation process.

Although specific embodiments have been illustrated and described, it will be obvious to those skilled in the art that various modifications may be made without departing from what is intended to be limited solely by the appended claims.

What is claimed is:

1. A copolymer said copolymer being polymerized from [2-(methacryloyloxy)ethyl]trimethylammonium chloride and methoxy poly(ethylene glycol) methacrylate has an average molecular weight between 400 and 600 Daltons and an amine percentage, and said amine percentage of the copolymer is between 30% and 50%.

2. The copolymer according to claim 1, wherein the methoxy poly(ethylene glycol) methacrylate has an average molecular weight of 500 Daltons.

3. A method for removing leukocytes from a blood sample, said method for removing leukocytes from a blood sample comprising:
   providing a blood sample containing leukocytes;
   providing a copolymer, wherein the copolymer being polymerized from an amine functional monomer and a poly(ethylene glycol) functional monomer, wherein the amine functional monomer has the following chemical structure:

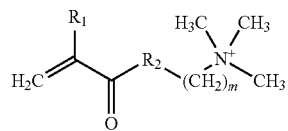

where
$R_1$ = H or $CH_3$;
$R_2$ = O or NH;
m = 1-5 and wherein the poly(ethylene glycol) functional monomer is selected from one or more of the group consisting of methoxy poly(ethylene glycol) methacrylate and methoxy poly(ethylene glycol) acrylate; and
treating the blood sample containing leukocytes with the copolymer, wherein the leukocytes adhere onto the surface of the copolymer so as to remove the leukocytes from the blood sample.

4. The method for removing leukocytes from a blood sample according to claim 3, wherein the copolymer being polymerized from [2-(methacryloyloxy)ethyl]trimethylammonium chloride and methoxy poly(ethylene glycol) methacrylate has an average molecular weight between 400 and 600 Daltons.

5. The method for removing leukocytes from a blood sample according to claim 1, wherein the copolymer being polymerized from [2-(methacryloyloxy)ethyl]trimethylammonium chloride and methoxy poly(ethylene glycol) methacrylate has an average molecular weight between 400 and 600 Daltons, and has an amine percentage being between 39% and 50%.

* * * * *